US009521952B2

(12) United States Patent
Miyasato (10) Patent No.: US 9,521,952 B2
(45) Date of Patent: Dec. 20, 2016

(54) PHOTOACOUSTIC IMAGING APPARATUS, PHOTOACOUSTIC IMAGING METHOD, AND PROGRAM

(75) Inventor: Takuro Miyasato, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/634,529

(22) PCT Filed: Mar. 14, 2011

(86) PCT No.: PCT/JP2011/056673
§ 371 (c)(1),
(2), (4) Date: Sep. 12, 2012

(87) PCT Pub. No.: WO2011/125468
PCT Pub. Date: Oct. 13, 2011

(65) Prior Publication Data
US 2013/0006089 A1 Jan. 3, 2013

(30) Foreign Application Priority Data
Apr. 8, 2010 (JP) .................................. 2010-089483

(51) Int. Cl.
*A61B 8/00* (2006.01)
*A61B 5/00* (2006.01)
(52) U.S. Cl.
CPC ........... *A61B 5/0073* (2013.01); *A61B 5/0095* (2013.01); *A61B 8/00* (2013.01)
(58) Field of Classification Search
USPC ....................................................... 600/407
See application file for complete search history.

(56) References Cited

U.S. PATENT DOCUMENTS 5,860,000 A * 1/1999 Biswas et al. ................. 712/244
2006/0264717 A1 * 11/2006 Pesach et al. ................. 600/310
(Continued)

FOREIGN PATENT DOCUMENTS

CN 101453939 A 6/2009
CN 101594819 A 12/2009
(Continued)

OTHER PUBLICATIONS

Charette et al., "An over view on recent radiation transport algorithm development for optical tomography imaging" Journal of Quantitative Spectroscopy & Radiative Transfer, Jun. 2008, pp. 2743-2766, vol. 109.
(Continued)

*Primary Examiner* — Tse Chen
*Assistant Examiner* — Lisa Kinnard
(74) *Attorney, Agent, or Firm* — Canon USA Inc., IP Division (57) ABSTRACT

A position of a light absorber existing in a subject and an initial sound pressure of an acoustic wave generated at the light absorber are calculated from an electric signal converted from the received acoustic wave generated in response to irradiation of the subject with light. An optical absorption coefficient and an optical scattering coefficient of the subject are calculated using the position of the light absorber and the initial sound pressure of the acoustic wave generated at the position of the light absorber. A light quantity distribution in the subject is calculated using the optical absorption coefficient and the optical scattering coefficient of the subject. An optical absorption coefficient distribution in the subject is calculated using the light quantity distribution in the subject and an initial sound pressure distribution in the subject obtained from the electric signal.

13 Claims, 5 Drawing Sheets (56) References Cited

U.S. PATENT DOCUMENTS

| | | | |
|---|---|---|---|
| 2008/0014574 A1* | 1/2008 | Viator | G01N 21/1702 |
| | | | 435/4 |
| 2008/0058638 A1* | 3/2008 | Zhu et al. | 600/425 |
| 2008/0221647 A1* | 9/2008 | Chamberland et al. | 607/88 |
| 2009/0069674 A1 | 3/2009 | Masumura et al. | |
| 2009/0227997 A1* | 9/2009 | Wang et al. | 606/10 |

FOREIGN PATENT DOCUMENTS

| | | |
|---|---|---|
| EP | 2002784 A1 | 12/2008 |
| JP | 2009-018153 A | 1/2009 |
| JP | 2009018153 A | 1/2009 |
| WO | WO 2009011934 A1 * | 1/2009 |
| WO | 2009/154244 A1 | 12/2009 |
| WO | WO 2010142530 A1 * | 12/2010 |

OTHER PUBLICATIONS

Rosenthal et al., "Quantitative Optoacoustic Signal Extraction Using Sparse Signal Representation" IEEE Transactions on Medical Imaging, Dec. 2009, pp. 1997-2006, vol. 28, No. 12.

Cox et al., "Quantitative Photoacoustic Image Reconstruction for Molecular Imaging", Proc. of SPIE, 2006, pp. 60861M-1-60861M-9, vol. 6086.

Cox et al.,"Two-dimensional quantitative photoacoustic image reconstruction of absorption distributions in scattering media by use of a simple iterative method", Applied Optics, Mar. 2006, pp. 1866-1875, vol. 45, No. 8.

Razansky, et al., Hybrid photoacoustic fluorescence molecular tomography using finite element based inversion, Am. Assoc. Phys. Med. 34 (11), Oct. 19, 2007, p. 4293-4301.

* cited by examiner

FIG. 5

PHOTOACOUSTIC IMAGING APPARATUS, PHOTOACOUSTIC IMAGING METHOD, AND PROGRAM

TECHNICAL FIELD

The present invention relates to photoacoustic imaging apparatuses, photoacoustic imaging methods, and programs.

BACKGROUND ART

Researches are positively conducted, mainly in the medical field, on imaging apparatuses that irradiate a subject with light from a light source, such as a laser, so that the light propagates in the subject and obtain information in the subject. As a type of such an imaging technique, photoacoustic tomography (PAT) has been proposed. PAT is a technique for visualizing information regarding optical properties in a living body (i.e., a subject) by irradiating the living body serving as the subject with pulsed light emitted from a light source, receiving an acoustic wave generated from a biological tissue having absorbed the light propagated and diffused in the living body, and analyzing the received acoustic wave. With this technique, biological information, such as a distribution of optical property values (hereinafter, referred to as an optical property value distribution) in the living body, particularly, a distribution of optical energy absorption densities (hereinafter, referred to as an optical energy absorption density distribution), can be obtained.

In PAT, an initial sound pressure $P_0$ of an acoustic wave generated from a light absorber existing in a subject can be represented by the following expression.

$$P_0 = \Gamma \cdot \mu_a \cdot \Phi \qquad \text{Expression 1,}$$

where $\Gamma$ denotes a Grüneisen coefficient, which is a result of dividing the product of a thermal coefficient of volume expansion or isobaric volume expansion coefficient ($\beta$) and a square of speed of light (c) by specific heat at constant pressure ($C_p$). It is known that the Grüneisen coefficient $\Gamma$ is substantially constant for a specific subject. $\mu_a$ denotes an optical absorption coefficient of the absorber, whereas $\Phi$ denotes a light quantity in a local region (i.e., a quantity of light that the absorber is irradiated with and also called the "optical fluence").

A change in sound pressure P representing the magnitude of the acoustic wave propagating in the subject is measured with respect to time and a distribution of the initial sound pressures (hereinafter, referred to as an initial sound pressure distribution) is calculated from the measurement result. A distribution of the product of $\mu_a$ and $\Phi$, i.e., the optical energy absorption density distribution, can be obtained by dividing the calculated initial sound pressure distribution by the Grüneisen coefficient $\Gamma$.

As indicated by Expression 1, in order to obtain the distribution of the optical absorption coefficients $\mu_a$ (hereinafter, referred to as an optical absorption coefficient distribution) from the distribution of the initial sound pressures $P_0$ (hereinafter, referred to as an initial sound pressure distribution), a distribution of the light quantities $\Phi$ (hereinafter, referred to as a light quantity distribution) in the subject has to be determined. Given that the light propagates in the subject like a plane wave when a region sufficiently large enough for thickness of the subject is irradiated with light of a uniform quantity, the light quantity distribution $\Phi$ in the subject can be represented by the following expression.

$$\Phi = \Phi_0 \cdot \exp(-\mu_{eff} \cdot d) \qquad \text{Expression 2,}$$

where $\mu_{eff}$ denotes an average effective attenuation coefficient of the subject, whereas $\Phi_0$ denotes a light quantity incoming from a light source to the subject (i.e., a light quantity on a surface of the subject). d denotes a distance between a region of the subject surface irradiated with the light emitted from the light source (i.e., a light irradiated region) and a light absorber existing in the subject. According to PTL1, a living body is irradiated with uniform light under a plurality of conditions and the average effective attenuation coefficient $\mu_{eff}$ of the subject is calculated. The light quantity distribution $\Phi$ in the subject is then calculated based on Expression 2. The light absorption coefficient distribution $\mu_a$ in the subject can be determined based on Expression 1 using the light quantity distribution $\Phi$.

CITATION LIST

Patent Literature

PTL 1 Japanese Patent Laid-Open No. 2009-18153

SUMMARY OF INVENTION

Technical Problem

However, it is difficult to accurately determine the light quantity distribution and the optical absorption coefficient distribution even with the method for calculating the average effective attenuation coefficient $\mu_{eff}$ of the subject disclosed in PTL1 unless the subject is irradiated with uniform light.

In view of the foregoing problem, the present invention makes it possible to accurately determine an optical property value distribution in a subject, particularly, an optical absorption coefficient distribution.

Solution to Problem

In accordance with an aspect of the present invention, a photoacoustic imaging apparatus includes: an acoustic wave converting unit configured to receive an acoustic wave generated in response to irradiation of a subject with light and convert the received acoustic wave into an electric signal; and a processing unit configured to generate image data from the electric signal. The processing unit calculates, from the electric signal, a position of a light absorber existing in the subject and an initial sound pressure of the acoustic wave generated at the light absorber, calculates an optical absorption coefficient and an optical scattering coefficient of the subject using the position of the light absorber and the initial sound pressure of the acoustic wave generated at the position of the light absorber, calculates a light quantity distribution in the subject using the optical absorption coefficient and the optical scattering coefficient of the subject, and generates image data of an optical absorption coefficient distribution in the subject using the light quantity distribution in the subject and an initial sound pressure distribution in the subject obtained from the electric signal.

In accordance with another aspect of the present invention, a photoacoustic imaging method for receiving an acoustic wave generated in response to irradiation of a subject with light, converting the received acoustic wave into an electric signal, and generating image data from the electric signal, includes: calculating, from the electric signal, a position of a light absorber existing in the subject and an initial sound pressure of the acoustic wave generated at the light absorber; calculating an optical absorption coefficient and an optical scattering coefficient of the subject using the position of the light absorber and the initial sound pressure of the acoustic wave generated at the position of the light absorber; calculating a light quantity distribution in the subject using the optical absorption coefficient and the optical scattering coefficient of the subject; and generating image data of an optical absorption coefficient distribution in the subject using the light quantity distribution in the subject and an initial sound pressure distribution in the subject obtained from the electric signal.

Advantageous Effects of Invention

In accordance with an aspect of the present invention, an optical property value distribution in a subject, particularly, an optical absorption coefficient distribution, can be accurately determined.

DESCRIPTION OF EMBODIMENTS

Exemplary embodiments of the present invention will be described below using the accompanying drawings. In exemplary embodiments of the present invention, an acoustic wave includes waves called a sonic wave, an ultrasonic wave, and a photoacoustic wave and indicates an elastic wave generated in a subject in response to irradiation of the subject with light (i.e., an electromagnetic wave), such as near-infrared radiation. Additionally, photoacoustic imaging apparatuses according to exemplary embodiments of the present invention are mainly for diagnosis of diseases of humans and animals, such as a malignant tumor and a blood vessel disease, and for follow-up of chemotherapy. The photoacoustic imaging apparatuses obtain information in the subject (hereinafter, referred to as subject information) and generate image data thereof. Accordingly, it is assumed that a diagnosis-target portion, such as a living body, more specifically, a breast, a finger, or a limb of a human body or an animal, serve as the subject. A light absorber existing in the subject has a relatively high optical absorption coefficient in the subject. For example, when a human body is subjected to measurement, oxidized or reduced hemoglobin, or a blood vessel including lots of oxidized or reduced hemoglobin, or a malignant tumor including many new blood vessels corresponds to the light absorber. The subject information indicates a distribution of sources of acoustic waves generated in response to light irradiation, an initial pressure distribution in the subject, or an optical energy absorption density distribution, an absorption coefficient distribution, and a density distribution of constituents of a tissue that are determined from the initial pressure distribution. The constituent density distribution includes, for example, an oxygen saturation distribution and an oxidized/reduced hemoglobin density distribution.

First Exemplary Embodiment

Figure 1A:
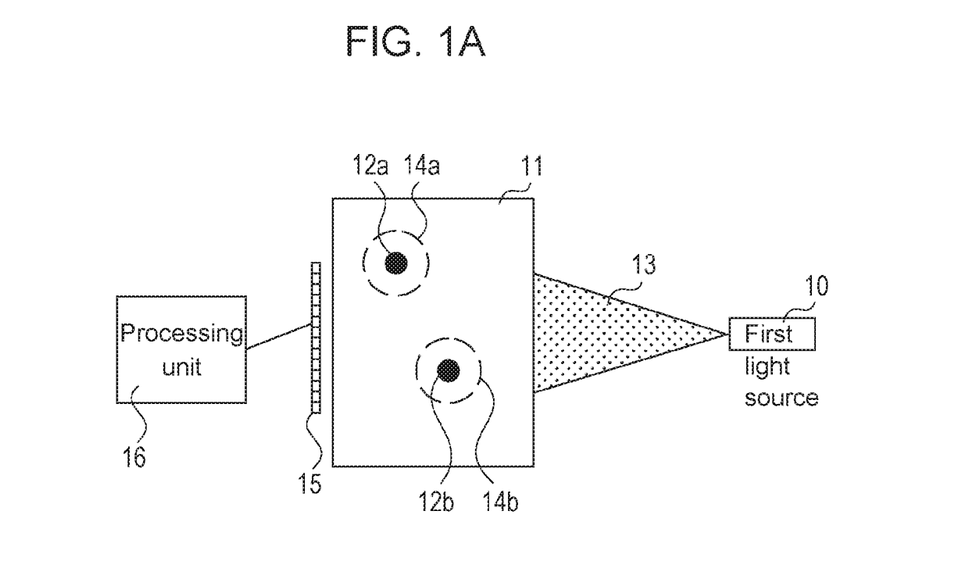
FIGS. 1A and 1B are schematic diagrams illustrating an example of a photoacoustic imaging apparatus according to a first exemplary embodiment of the present invention.
Figure 1B:
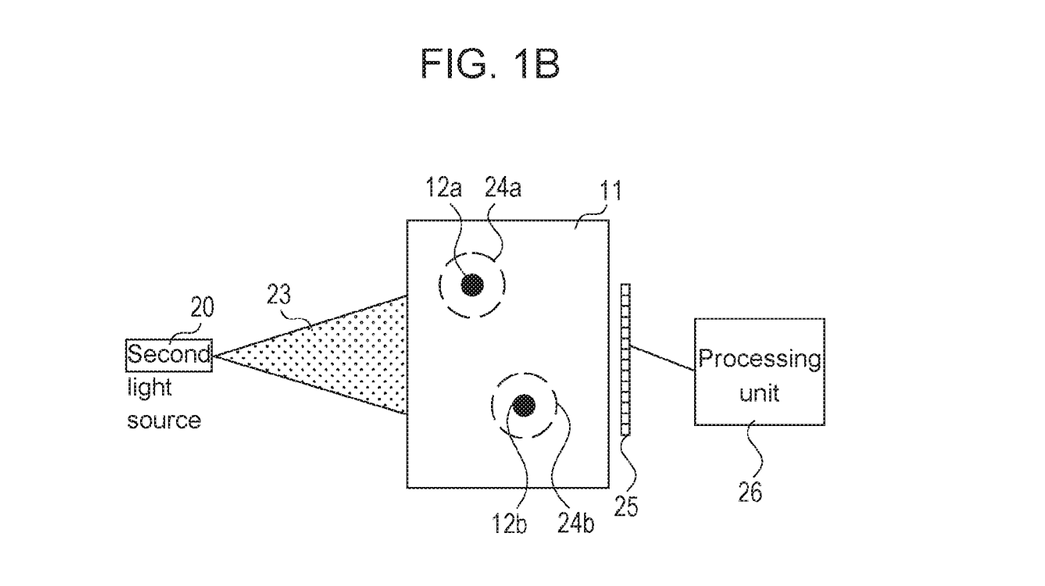

FIGS. 1A and 1B illustrate a configuration of a photoacoustic imaging apparatus according to a first exemplary embodiment. The photoacoustic imaging apparatus according to the first exemplary embodiment includes an acoustic wave converting unit 15 (25) and a processing unit 16 (26). Referring to FIGS. 1A and 1B, positions of light sources are changed so that directions of irradiating a subject with light differ from one another. More specifically, a subject 11 is irradiated with light 13 from a right side of the subject 11 on the paper in FIG. 1A, whereas the subject 11 is irradiated with light 23 from a left side of the subject 11 on the paper in FIG. 1B. Additionally, referring to FIG. 1B, the subject 11 may be irradiated with the light 23 from an upper side or a lower side of the subject 11 on the paper.

PAT measurement performed by the photoacoustic imaging apparatus according to the first exemplary embodiment will be described using FIG. 1A. The subject 11, such as a living body, is irradiated with the light 13 emitted from a first light source 10. Once part of energy of the light having propagated in the subject 11 is absorbed by light absorbers 12a and 12b (eventually serving as sound sources) in a blood vessel, blood, or the like, thermal expansion of the light absorbers 12a and 12b generates acoustic waves 14a and 14b (typically, ultrasonic waves), respectively. The acoustic waves 14a and 14b are received and converted into electric signals by the acoustic wave converting unit 15. The processing unit 16 then performs analytic processing on the electric signals to generate data, such as an optical property value distribution of the subject 11. The analytic processing includes processing for calculating an optical absorption coefficient and an optical scattering coefficient of the subject and calculating a light quantity distribution of the subject using the calculated coefficients. The analytic processing will be described more specifically later. The optical absorption coefficient and the optical scattering coefficient of the subject indicate those obtained when it is assumed that the subject is a substance having a constant optical absorption coefficient and a constant optical scattering coefficient, respectively. That is, the optical absorption coefficient and the optical scattering coefficient of the subject can be referred to as an average optical absorption coefficient and an average optical scattering coefficient, respectively.

After an initial sound pressure distribution $P_1(r)$ of the sound source of the acoustic waves generated in the subject 11 is generated as the optical property value distribution, positions $r_a$ and $r_b$ of the light absorbers 12a and 12b are determined from the initial sound pressure distribution, respectively. More specifically, as described above, since the light absorber has a relatively high optical absorption coefficient in the subject, the initial sound pressure that is proportional to the optical absorption coefficient is also high in the subject. Thus, a position showing an initial sound pressure that is equal to or higher than a predetermined threshold is specified as a position of the light absorber (i.e., a sound source) based on the initial sound pressure distribution. Although the description will be given below for a case of specifying positions of two light absorbers, the number of the light absorbers may be two or more or may be one. In particular, since the optical absorption coefficient and the optical scattering coefficient of the subject, and thus, the light quantity distribution can be preferably determined more accurately as the number of light absorbers subjected to the position specification increases. Additionally, the threshold may be larger than zero and capable of specifying at least one position. The position "r" may be relative to a predetermined position on or in the subject 11 or relative to a predetermined position on the light source or the acoustic wave converting unit. In addition, even when the criterion (e.g., the light source) is movable, the position "r" can be determined as a relative position with respect to the criterion.

Initial sound pressures $P_{1a}$ and $P_{1b}$ of the acoustic waves 14a and 14b generated from the light absorbers 12a and 12b existing in the subject 11 in response to irradiation of the subject 11 with the light 13 emitted from the first light source 10 can be represented by the following expression, respectively.

[Math. 1]

$$P_{1a}=\Gamma\cdot\mu_a^{Ta}\cdot\Phi_{1a},\ P_{1b}=\Gamma\cdot\mu_a^{Tb}\cdot\Phi_{1b} \qquad \text{Expression 3}$$

Here, $\Gamma$ denotes a Grüneisen coefficient of the light absorber, $\mu_a^{Ta}$ denotes an optical absorption coefficient of the light absorber 12a, and $\mu_a^{Tb}$ denotes an optical absorption coefficient of the light absorber 12b. Additionally, $\Phi_{1a}$ denotes a local light quantity at the position $r_a$ of the light absorber 12a irradiated from the first light source 10, whereas $\Phi_{1b}$ denotes a local light quantity at the position $r_b$ of the light absorber 12b irradiated from the first light source 10.

Since the Grüneisen coefficient $\Gamma$ of the light absorber is substantially uniquely determined for a specific tissue, the product of the optical absorption coefficient and the light quantity (i.e., an optical energy absorption density) of each of the light absorbers 12a and 12b can be determined based on Expression 3.

Additionally, a light quantity distribution $\Phi_1(r)$ in the subject 11 when the light is emitted from the first light source 10 can be determined by the following expression (i.e., a diffusion equation).

[Math. 2]

$$-\vec{\nabla}_r \kappa^B \nabla_r \Phi_1(\vec{r}) + \mu_a^B \Phi_1(\vec{r}) = q_1(\vec{r}) \qquad \text{Expression 4}$$

Here, $\kappa^B$ denotes an optical diffusion coefficient of the subject, whereas $\mu_a^B$ denotes an optical absorption coefficient of the subject. $\kappa^B$ is equal to $1/(3(\mu_a^B + \mu_s'^B))$, where $\mu_s'^B$ denotes an optical scattering coefficient of the subject. The optical absorption coefficient $\mu_a^B$ of the subject and the optical scattering coefficient $\mu_s'^B$ of the subject are constants independent from the position "r". Additionally, $q_1(r)$ denotes an illumination distribution on a surface of the subject 11 when the subject 11 is irradiated from the first light source 10. At the positions $r_a$ and $r_b$ of the light absorbers 12a and 12b, $\Phi_{1a}=\Phi_1(r_a)$ and $\Phi_{1b}=\Phi_1(r_b)$ are satisfied, respectively. To solve Expression 4, the optical absorption coefficient $\mu_a^B$ of the subject and the optical scattering coefficient $\mu_s'^B$ of the subject have to be determined. The optical absorption coefficient and the optical scattering coefficient of the subject can be estimated based on constituents of and a distribution in a tissue of the subject if the subject is specified. However, since the values thereof are affected by an individual difference of the subject, the estimated optical absorption coefficient and optical scattering coefficient of the subject are desirably determined for each measurement.

To this end, in this exemplary embodiment, as illustrated in FIG. 1B, PAT measurement is performed at a different time point under an irradiation condition different from that illustrated in FIG. 1A. More specifically, referring to FIG. 1B, the subject 11 is irradiated with the light 23 emitted from a second light source 20 provided at a position different from the first light source 10. In such a way, in this exemplary embodiment, the subject is irradiated with light under the irradiation conditions different from one another at time points different from one another. The subject 11 is irradiated with the light 23 emitted from the second light source 20. The acoustic wave converting unit 25 receives acoustic waves 24a and 24b. The processing unit 26 receives electric signals converted from the acoustic waves by the acoustic wave converting unit 25 and generates image data. The light source 20, the acoustic wave converting unit 25, and the processing unit 26 may be the same as or different from those illustrated in FIG. 1A. That is, any given configuration may be used in FIGS. 1A and 1B as long as the direction of irradiating the subject 11 with the light differs. The PAT measurement illustrated in FIGS. 1A and 1B is performed at different time points. More specifically, the PAT measurement illustrated in FIG. 1B may be performed after the PAT measurement illustrated in FIG. 1A or the order may be switched. When the PAT measurement illustrated in FIG. 1B is performed at a time point different from that of the PAT measurement illustrated in FIG. 1A, the first light source 10 in FIG. 1A may be arranged at the same position as illustrated in FIG. 1A and the PAT measurement may be performed with the subject 11 being irradiated with the light 13 from the first light source 10. That is, the PAT measurement illustrated in FIGS. 1A and 1B may be simultaneously performed at a time point different from that of the PAT measurement illustrated in FIG. 1A.

By performing the PAT measurement similar to that illustrated in FIG. 1A, image data of an optical property value distribution of the subject 11 is obtained. As a result, an initial sound pressure distribution $P_2(r)$ of a sound source of the acoustic wave generated in the subject 11 is obtained. Initial pressures at the positions $r_a$ and $r_b$ of the light absorbers 12a and 12b are determined based on the initial sound pressure distribution, respectively. Meanwhile, since the positions $r_a$ and $r_b$ are determined in the PAT measurement illustrated in FIG. 1A, the positions do not have to be determined again.

Initial sound pressures $P_{2a}$ and $P_{2b}$ of the acoustic waves 24a and 24b generated from the light absorbers 12a and 12b in the subject 11 in response to irradiation of the subject 11 with the light 23 from the second light source 20 can be represented by the following expression, respectively.

[Math. 3]

$$P_{2a}=\Gamma\cdot\mu_a^{Ta}\cdot\Phi_{2a},\ P_{2b}=\Gamma\cdot\mu_a^{Tb}\cdot\Phi_{2b} \qquad \text{Expression 5}$$

Here, $\Phi_{2a}$ denotes a local light quantity at the position $r_a$ of the light absorber 12a irradiated from the second light source 20, whereas $\Phi_{2b}$ represents a local light quantity at the position $r_b$ of the light absorber 12b irradiated from the second light source 20. As understood from FIGS. 1A and 1B, since a position of the light illuminating the surface of the subject 11 from the first light source 10 differs from a position of the light illuminating the surface of the subject 11 from the second light source 20, the illumination distributions $q_1(r)$ and $q_2(r)$ on the surface of the subject 11 differ from one another. Thus, the local light quantities $\Phi_{1a}$ and $\Phi_{2a}$ (or $\Phi_{1b}$ and $\Phi_{2b}$) absorbed by the light absorber 12a (or 12b) differ from one another and the initial sound pressures $P_{1a}$ and $P_{2a}$ (or $P_{1b}$ and $P_{2b}$) also differ from one another, respectively.

In addition, the light quantity distribution $\Phi_2(r)$ in the subject 11 irradiated with the light 23 from the second light source 20 can be determined by the following expression. Meanwhile, the light quantity distributions $\Phi_1(r)$ and $\Phi_2(r)$ differ from one another.

[Math. 4]

$$-\vec{\nabla_s}\kappa^B\vec{\nabla_s}\Phi_2(\vec{r})+\mu_a^B\Phi_2(\vec{r})=q_2(\vec{r}) \qquad \text{Expression 6}$$

Here, $q_2(r)$ denotes an illumination distribution on the surface of the subject 11 irradiated from the second light source 20. At the positions $r_a$ and $r_b$ of the light absorbers 12a and 12b, $\Phi_{2a}=\Phi_2(r_a)$ and $\Phi_{2b}=_2(r_b)$ are satisfied, respectively. To solve Expression 6, the optical absorption coefficient $\mu_a^B$ of the subject and the optical scattering coefficient $\mu_s^{\prime B}$ of the subject have to be determined just like Expression 4.

A method for determining the optical absorption coefficient and the optical scattering coefficient of the subject will now be described. Temporary values (e.g., values of a constituent having the largest weight ratio in a tissue of the subject subjected to the measurement) are substituted for $\mu_a^B$ and $\mu_s^{\prime B}$ of Expression 4 and Expression 6 to solve Expression 4 and Expression 6 using a finite element method or the like and determine the light quantity distributions $\Phi_1(r)$ and $\Phi_2(r)$. To determine whether the calculated light quantity distributions $\Phi_1(r)$ and $\Phi_2(r)$ are correct, the initial sound pressures $P_{1a}$, $P_{1b}$, $P_{2a}$, and $P_{2b}$ of the light absorbers 12a and 12b are utilized. A detail will be described below.

First, unknown values $\mu_a^{Ta}$ and $\mu_b^{Tb}$ serving as the optical absorption coefficients of the light absorbers 12a and 12b are eliminated by dividing the first equation and the second equation of Expression 5 by the first equation and the second equation of Expression 3, respectively. As a result, the following expression is obtained.

[Math. 5]

$$\frac{P_{2a}}{P_{1a}}=\frac{\Phi_{2a}}{\Phi_{1a}},\ \frac{P_{2b}}{P_{1b}}=\frac{\Phi_{2b}}{\Phi_{1b}} \qquad \text{Expression 7}$$

Here, the left sides of two equations of Expression 7 are constituted by the initial sound pressures $P_{1a}$, $P_{1b}$, $P_{2a}$, and $P_{2b}$ of the light absorbers 12a and 12b, which are analyzed from the electric signals converted from the acoustic waves by the acoustic wave converting unit and are obtained from the PAT measurement. On the other hand, the right sides of the two equation of Expression 7 are constituted by the local light quantities $\Phi_{1a}$, $\Phi_{1b}$, $\Phi_{2a}$, and $\Phi_{2b}$ at the positions $r=r_a$ and $r=r_b$ of the light absorbers 12a and 12b in the calculated light quantity distributions $\Phi_1(r)$ and $\Phi_2(r)$, respectively. These values are not determined from the PAT measurement but calculated by solving Expression 4 and Expression 6 as described above. That is, since Expression 7 is satisfied in the actual subject, solutions of Expression 4 and Expression 6 are substituted in the right sides of the two equations of Expression 7 to determine whether the left side and the right side of each of the two equations of Expression 7 are equal.

Accordingly, Expression 4 and Expression 6 are solved using an objective function f represented by the following expression by substituting different values for $\mu_a^B$ and $\mu_s^{\prime B}$ until the objective function f becomes equal to zero or a value that can be considered as zero (e.g. equal to or smaller than $1.0\times10^{-6}$) to obtain other $\Phi_1(r)$ and $\Phi_2(r)$. The values of $\mu_a^B$ and $\mu_s^{\prime B}$ determined when the objective function f is equal to zero or the value that can be considered as zero are calculated as actual optical absorption coefficient and optical scattering coefficient of the subject.

[Math. 6]

$$f=\sqrt{\left(\frac{P_{2a}}{P_{1a}}-\frac{\Phi_{2a}}{\Phi_{1a}}\right)^2+\left(\frac{P_{2b}}{P_{1b}}-\frac{\Phi_{2b}}{\Phi_{1b}}\right)^2} \qquad \text{Expression 8}$$

The solutions $\Phi_1(r)$ and $\Phi_2(r)$ of Expression 4 and Expression 6 solved using the values of the optical absorption coefficient and the optical scattering coefficient of the subject calculated in this manner are light quantity distributions in the subject illustrated in FIGS. 1A and 1B, respectively. The optical absorption coefficients $\mu_a^{Ta}$ and $\mu_b^{Tb}$ of the light absorbers 12a and 12b, respectively, can be then determined based on Expression 3 or Expression 5.

Figure 2:
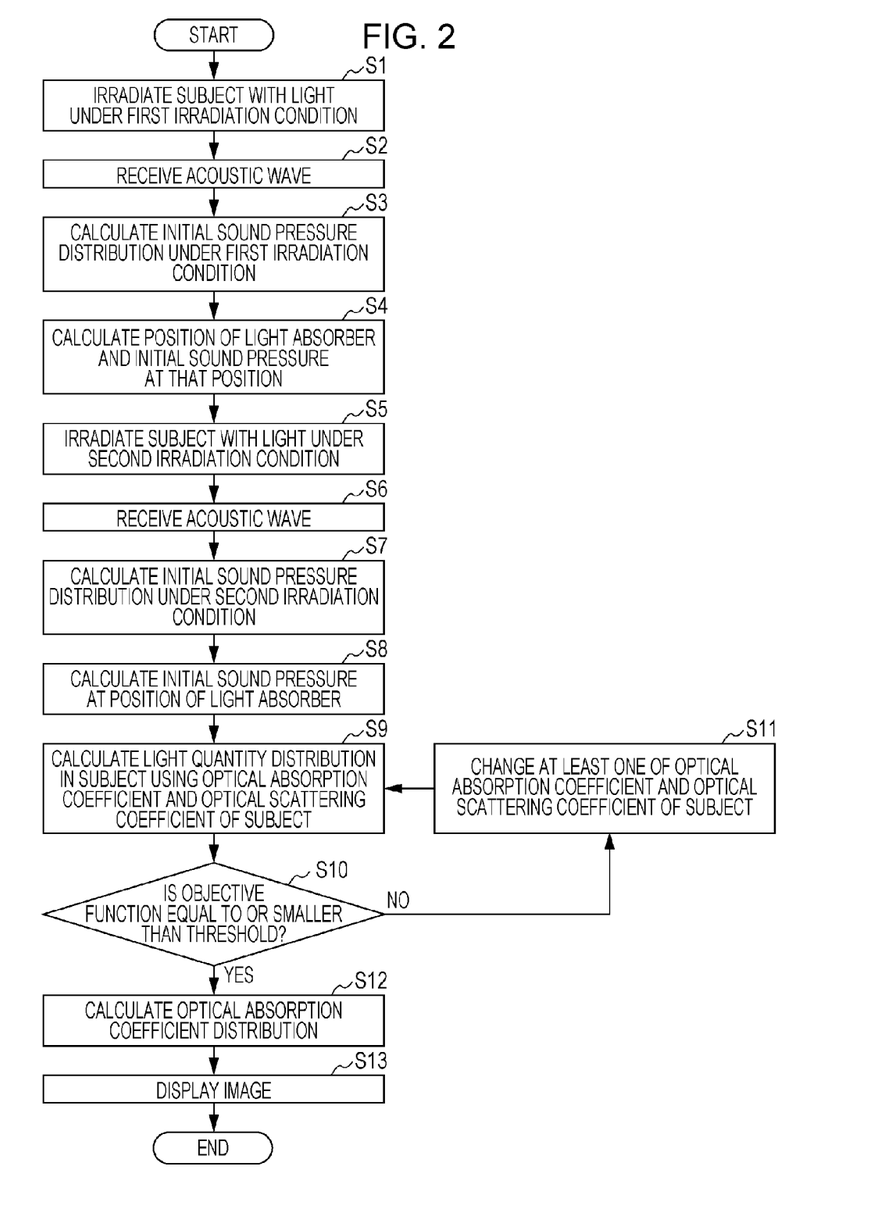
FIG. 2 is a flowchart describing a photoacoustic imaging method according to the first exemplary embodiment of the present invention.

FIG. 2 illustrates a flowchart according to this exemplary embodiment.

First, the light 13 is emitted with the first light source 10 facing the acoustic wave converting unit 15 through the subject 11 (i.e., a first irradiation condition) as illustrated in FIG. 1A (S1). The acoustic wave converting unit 15 receives the acoustic waves 14a and 14b generated from the light absorbers 12a and 12b existing in the subject 11 because of an optoacoustic effect (S2). The acoustic wave converting unit 15 converts the received acoustic waves into electric signals. The processing unit 16 loads the electric signals. The processing unit 16 then performs analytic processing on the electric signals to calculate the initial sound pressure distribution $P_1(r)$ (S3). The processing unit 16 then extracts two points having values equal to or larger than a threshold from the initial sound pressure distribution $P_1(r)$ obtained in STEP S3 and calculates the positions $r=r_a$ and $r_b$ thereof and the initial sound pressures $P_{1a}$ and $P_{1b}$ at the positions, respectively (S4).

The light 23 is then emitted with the second light source 20 facing the acoustic wave converting unit 25 through the subject 11 (i.e., a second irradiation condition different from the first one) as illustrated in FIG. 1B (S5). The acoustic wave converting unit 25 receives the acoustic waves 24a and 24b generated from the light absorbers 12a and 12b (S6). The acoustic wave converting unit 25 converts the received acoustic waves into electric signals. The processing unit 26 loads the electric signals. The processing unit 26 then performs analytic processing on the electric signals to calculate the initial sound pressure distribution $P_2(r)$ (S7). The processing unit 26 calculates the initial sound pressures $P_{2a}$ and $P_{2b}$ at the positions $r=r_a$ and $r_b$ from the initial sound pressure distribution $P_2(r)$ obtained in STEP S7, respectively (S8).

The light quantity distribution $\Phi_1(r)$ in the subject under the first irradiation condition and the light quantity distribution $\Phi_2(r)$ in the subject under the second irradiation condition are calculated by solving Expression 4 and Expression 6 (S9). Here, temporary values are used for the optical absorption coefficient $\mu_a^B$ of the subject and the optical scattering coefficient $\mu_s^{\prime B}$ of the subject. Furthermore, known measured values are used for the illumination distribution $q_1(R)$ on the surface of the subject under the first irradiation condition and the illumination distribution $q_2(r)$ on the surface of the subject under the second irradiation condition.

The values $\Phi_{1a}$, $\Phi_{1b}$, $\Phi_{2a}$, and $\Phi_{2b}$ at the positions $r=r_a$ and $r_b$ are determined from the light quantity distributions $\Phi_1(r)$ and $\Phi_2(r)$ calculated in STEP S9, a value of the objective function f denoted by Expression 8 is calculated, and the resulting value is examined (S10). More specifically, it is determined whether the value of the objective function f is equal to or smaller than a value that can be considered as zero.

If the value of the objective function f exceeds a predetermined threshold, at least one of the values of $\mu_a^B$ and $\mu_s'^B$ is changed to decrease the value of the objective function f (S11). STEPs S9 and S10 are then performed using the other value. STEPs S11, S9, and S10 are repeated until the value of the objective function f becomes equal to or smaller than the predetermined threshold.

If the value of the objective function f is equal to or smaller than the predetermined threshold in STEP S10, the values $\mu_a^B$, $\mu_s'^B$, $\Phi_1(r)$, $\Phi_2(r)$, $\Phi_{1a}$, $\Phi_{1b}$, $\Phi_{2a}$, and $\Phi_{2b}$ at that time are calculated. The optical absorption coefficient of the light absorber and the optical absorption coefficient distribution in the subject are calculated from these values and Expressions 3 to 6 (S12).

The optical absorption coefficient distribution is obtained as image data. The image data is displayed as an image on a display device (S13).

A configuration of the photoacoustic imaging apparatus according to this exemplary embodiment will now be described more specifically.

The acoustic wave converting unit includes one or more elements for receiving an acoustic wave and converting the acoustic wave into an electric signal, such as a transducer based on piezoelectric effects, a transducer based on optical resonance, and a transducer based on capacitance change. Any given element can be used as long as the element can receive the acoustic wave and convert the acoustic wave into an electric signal. Since the acoustic wave can be simultaneously received at a plurality of positions by one-dimensionally or two-dimensionally arranging a plurality of elements receiving the acoustic waves, reception time can be shortened and an effect of vibration of the subject can be reduced. Meanwhile, a signal similar to that resulting from one-dimensional or two-dimensional arrangement of the plurality of elements can be obtained by moving one element. Additionally, an acoustic impedance matching medium, such as gel, is preferably applied between the acoustic wave converting unit and the subject to suppress reflection of the acoustic waves.

The processing unit may have any given configuration as long as the processing unit can store intensity of the acoustic wave and a change of the intensity with respect to time and convert the stored information into data of an optical property value distribution with an arithmetical unit thereof. For example, an oscilloscope and a computer capable of analyzing data stored in the oscilloscope can be used. Additionally, a workstation or the like is used as the processing unit and image reconstruction processing (i.e., processing for generating image data) is performed by software programmed in advance. For example, the software used in the workstation includes a signal processing module for performing electric-signal amplification processing and noise reduction processing and an image reconstruction module for performing image reconstruction. Meanwhile, in PAT, preprocessing, such as the noise reduction processing, is generally performed on a signal received at each position prior to the image reconstruction. The signal processing module preferably performs such preprocessing. Additionally, the image reconstruction module performs formation of image data based on image reconstruction and uses, for example, time-domain or Fourier-domain back projection generally used in the tomography technique as an image reconstruction algorithm.

Figure 5:
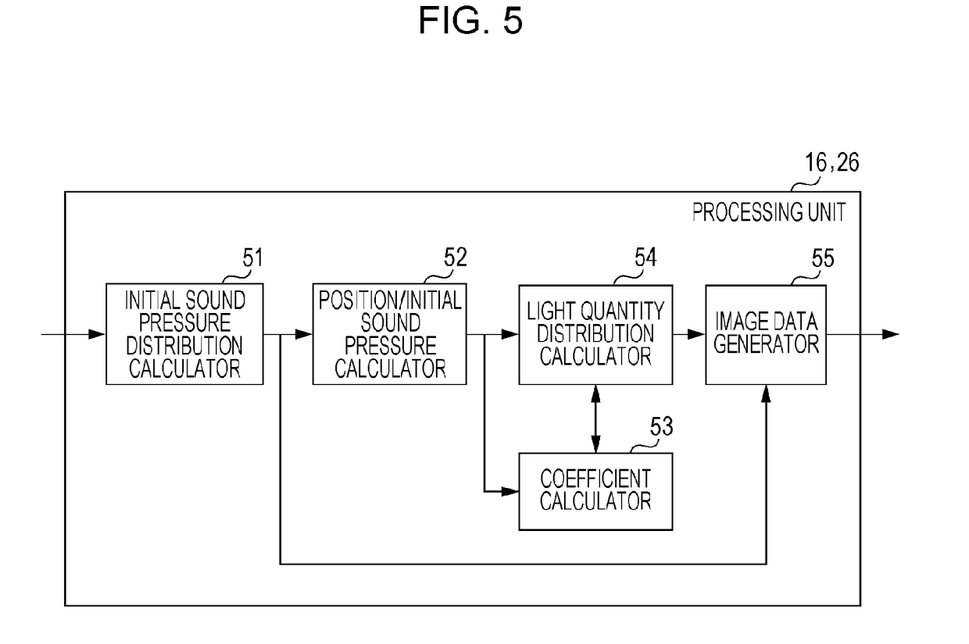
FIG. 5 is a block diagram illustrating an example of a processing unit of the photoacoustic imaging apparatus according to the first exemplary embodiment of the present invention.

In addition, as illustrated in FIG. 5, the processing unit 16 (26) may include an initial sound pressure distribution calculator 51, a position/initial sound pressure calculator 52 for calculating the position of the light absorber and the initial pressure at the position, and a coefficient calculator 53 for calculating the optical absorption coefficient and the optical scattering coefficient in the subject. The processing unit 16 (26) may further include a light quantity distribution calculator 54 and an image data generator 55. The initial sound pressure distribution calculator 51 performs STEPs S3 and S7 in the above-described flowchart to calculate the initial sound pressure distribution from the electric signals output from the acoustic wave converting unit 15 (25). The position/initial sound pressure calculator 52 performs STEPs S4 and S8 in the above-described flowchart to calculate the position of the light absorber and the initial sound pressure of the acoustic wave generated at the light absorber on the basis of the initial sound pressure distribution calculated by the initial sound pressure distribution calculator 51. The coefficient calculator 53 performs STEPs S10 and S11 in the above-described flowchart to calculate the optical absorption coefficient and the optical scattering coefficient in the subject utilizing the position of the light absorber and the initial sound pressure of the acoustic wave generated at the light absorber calculated by the position/initial sound pressure calculator 52. The light quantity distribution calculator 54 performs STEP S9 in the above-described flowchart using the optical absorption coefficient and the optical scattering coefficient in the subject calculated by the coefficient calculator 53 to calculate the light quantity distribution in the subject. The image data generator 55 performs STEP S12 in the above-described flowchart on the basis of the light quantity distribution in the subject calculated by the light quantity distribution calculator 54 and the initial sound pressure distribution calculated by the initial sound pressure distribution calculator 51 to calculate the optical absorption coefficient distribution and generate image data of the optical absorption coefficient distribution.

When the light source is capable of emitting light of a plurality of wavelengths and irradiating the subject with the light of the plurality of wavelengths, a density distribution of constituents of the subject can be visualized using an optical property value distribution in the subject that changes depending on each wavelength. For example, by calculating the optical absorption coefficient distribution corresponding to each wavelength and comparing a value thereof with wavelength dependency unique to the constituents (such as glucose, collagen, or oxidized/reduced hemoglobin) of the subject tissue, the density distribution of the constituents of the subject may be visualized.

Meanwhile, the image data is data representing the subject information regardless of whether the image data is in the two-dimension or the three-dimension. The two-dimensional image data is constructed by arranging a plurality of pieces of pixel data, whereas the three-dimensional image data is constructed by arranging a plurality of pieces of voxel data. The pixel data and the voxel data are obtained by performing image reconstruction on acoustic waves obtained at plurality of positions. Although a description will be given for the three-dimensional image data below, the present invention can also applied to the two-dimensional image data.

The light source emits light of a specific wavelength to be absorbed by a specific constituent (e.g., hemoglobin) of constituents of the subject. More specifically, the wavelength of the light is preferably equal to or longer than 400 nm and equal to or shorter than 1600 nm because an acoustic wave generated at a light absorber (e.g., hemoglobin) existing in the subject is more easily discriminated from an acoustic wave generated on the surface (e.g., skin) of the subject in processing to be described later. At least one light source capable of emitting pulsed light of 5 nanoseconds to 50 nanoseconds is included. Although a laser capable of yielding a large output is preferably used as the light source, a light emitting diode (LED) or the like may be used instead of the laser. Various lasers, such as a solid-state laser, a gas laser, a dye laser, and a semiconductor laser, can be used. To measure the wavelength-dependent optical absorption coefficient distribution, a light source capable of emitting light of different wavelengths may be used instead of that emitting light of a single wavelength. In such a case, a laser using dyes or optical parametric oscillators (OPO) capable of changing the emitted wavelength can be used. Additionally, the light may be emitted from a side of the acoustic wave converting unit or from a side opposite to the acoustic wave converting unit. Furthermore, the light may be emitted from both sides of the subject.

When it is difficult to arrange each light source near the subject, a light irradiation part may be guided to the subject using an optical transmission line, such as an optical fiber. Although two light sources are used in FIGS. 1A and 1B, light may be emitted by one light source from different positions using an optical path converter, such as a mirror.

Figure 3A:
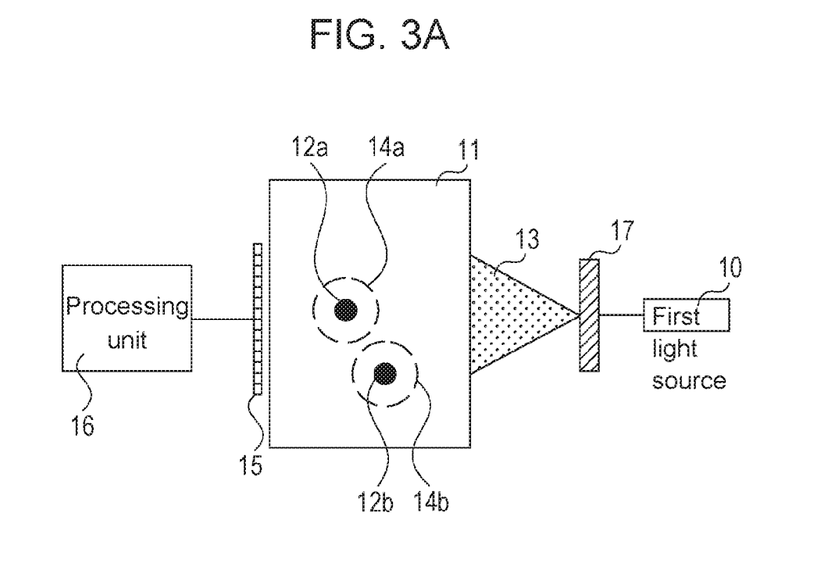
FIGS. 3A and 3B are schematic diagrams illustrating another example of the photoacoustic imaging apparatus according to the first exemplary embodiment of the present invention.
Figure 3B:
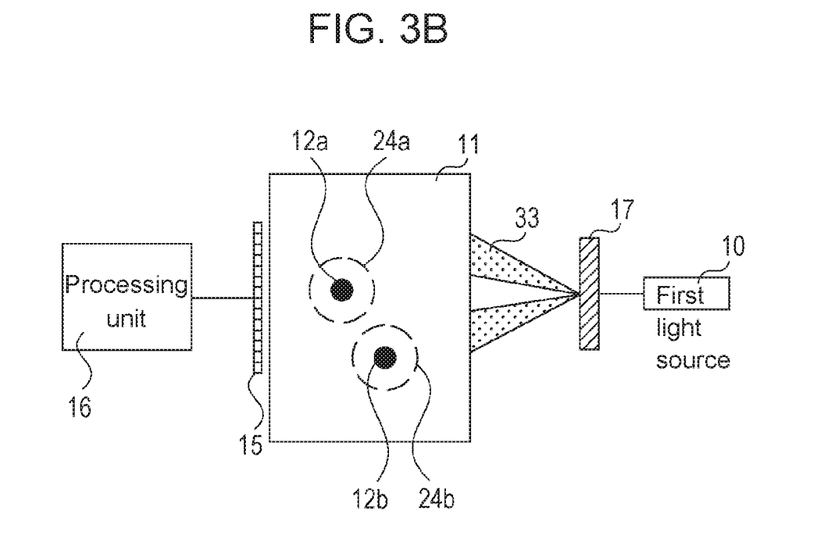

Alternatively, as illustrated in FIGS. 3A and 3B, the light 13 in FIG. 3A and light 33 in FIG. 3B are emitted from the same position by one light source. Illumination distributions of the light 13 and the light 33 on the surface of the subject are set to differ from one another through an optical system 17, such as a mask, arranged on an optical path. In this case, since the irradiation conditions of the light that the subject is irradiated with and the irradiation time points differ in FIGS. 3A and 3B, the diffusion equation can be formed under each condition and the optical absorption coefficient of the light absorber can be determined with the above-described method.

Figure 4A:
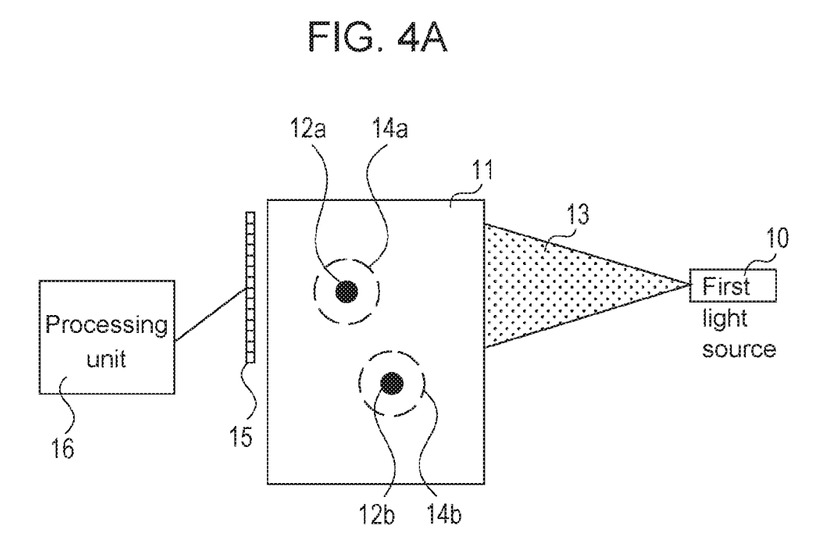
FIGS. 4A and 4B are schematic diagrams illustrating still another example of the photoacoustic imaging apparatus according to the first exemplary embodiment of the present invention.
Figure 4B:
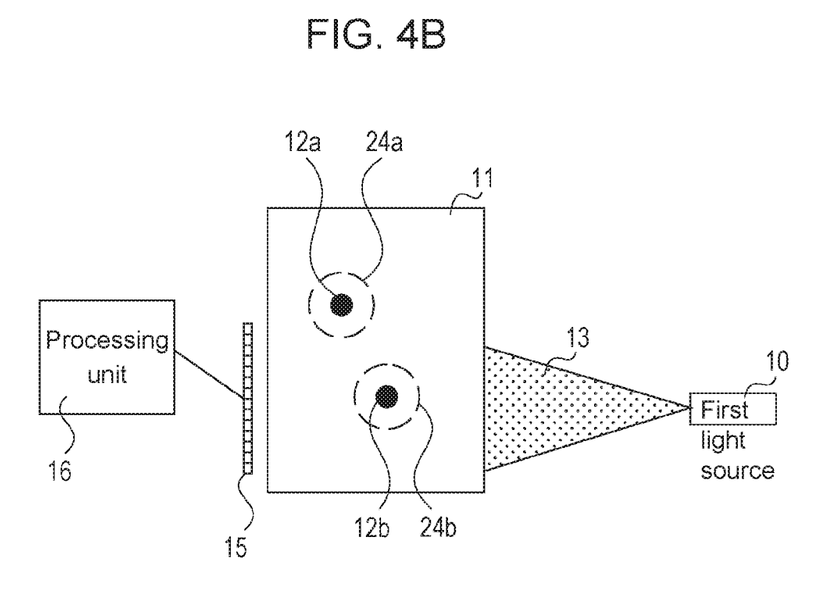

Additionally, as illustrated in FIGS. 4A and 4B, the acoustic wave converting unit 15 and the light source 10 may be synchronously moved with respective to the subject using a scanning unit (not illustrated). In this case, positions of the surface of the subject irradiated with light during the PAT measurement performed at different time points differ from one another. Since the irradiation conditions of the light that the subject is irradiated with and the illumination time points differ in FIGS. 4A and 4B, the diffusion equation can be formed under each condition and the optical absorption coefficient of the light absorber can be determined with the above-described method.

To carry out the present invention, at least one of the light irradiation direction, the illumination distribution on the surface of the subject, and the position of the surface of the subject irradiated with the light of the light irradiation condition may be set to differ in the PAT measurement performed at different time points.

Additionally, all of points where initial sound pressure is observed under the first irradiation condition and the second irradiation condition, i.e., all of light absorbers, may be used.

In this case, as many equations as the number of light absorbers are formed regarding Expression 3 or 5. The objective function f is represented as follows.

[Math. 7]

$$f = \sqrt{\left(\frac{P_{2a}}{P_{1a}} - \frac{\Phi_{2a}}{\Phi_{1a}}\right)^2 + \left(\frac{P_{2b}}{P_{1b}} - \frac{\Phi_{2b}}{\Phi_{1b}}\right)^2 + \left(\frac{P_{2c}}{P_{1c}} - \frac{\Phi_{2c}}{\Phi_{1c}}\right)^2 + \left(\frac{P_{2d}}{P_{1d}} - \frac{\Phi_{2d}}{\Phi_{1d}}\right)^2 + \ldots}$$

Expression 9

Here, $P_{ix}$ denotes an initial sound pressure of a light absorber located at a position $r_x$ measured under the i-th irradiation condition. In this case, values of $\mu_a^B$ and $\mu_s^{'B}$ obtained when this objective function f is equal to zero or a value that can be considered as zero are determined as the optical absorption coefficient and the optical scattering coefficient of the subject, respectively. As is clear from the objective function, the more the light absorbers, the more accurately the optical absorption coefficient and the optical scattering coefficient of the subject can be determined.

When the PAT measurement is performed using three or more light sources, more diffusion equations are obtained, the number of equations of Expression 3 or 5 increases, and the values of $\mu_a^B$ and $\mu_s^{'B}$ obtained when the objective function f is substantially equal to zero approach correct values. Thus, the optical absorption coefficient of the subject can be determined more accurately. The use of three or more light sources equates to performing the PAT measurement under three or more irradiation conditions. When three or more different illumination distributions on the surface of the subject are used with one light source, similar advantages can be obtained.

The light absorber may be a tumor and a blood vessel existing in the subject, or a similar substance in the subject that absorbs light, thermally expands by energy of the absorbed light, and generates an acoustic wave. Additionally, when a molecular probe is used as the light absorber, indocyanine green (ICG) is generally selected. However, any given substance may be used as long as the substance emits, in response to light irradiation, an acoustic wave larger than those of the subject substances therearound.

Second Exemplary Embodiment

The present invention is also realized by executing the following processing. More specifically, software (i.e., a program) realizing the functions of the above-described first exemplary embodiment is supplied to a system or an apparatus via a network or various storage media. A computer (or a central processing unit (CPU) or a microprocessing unit (MPU)) of the system or the apparatus reads out and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-089483, filed Apr. 8, 2010, which is hereby incorporated by reference herein in its entirety.

REFERENCE SIGNS LIST 11 subject
12a, 12b light absorber 13, 23 light
14a, 14b acoustic wave
15 acoustic wave converting unit
16 processing unit

The invention claimed is:

1. A subject information acquisition apparatus comprising:
an acoustic wave detector configured to receive a first acoustic wave generated in response to irradiation of a subject with first light having a certain wavelength and convert the received first acoustic wave into a first electric signal and configured to receive a second acoustic wave generated in response to irradiation of the subject with second light having the certain wavelength whose irradiation condition and irradiation time point are different from that of the first light and convert the received second acoustic wave into a second electric signal; and
a processor configured to acquire an optical absorption coefficient and an optical scattering coefficient of the subject by using the first electric signal and the second electric signal, configured to acquire a light intensity distribution of the first light in the subject based on the optical absorption coefficient and the optical scattering coefficient of the subject acquired by using the first electric signal and the second electric signal, and configured to acquire information of the subject related to an optical absorption coefficient distribution in the subject by using the first electrical signal and the light intensity distribution of the first light in the subject,
wherein the irradiation condition is at least one of a direction of light irradiation, an illumination distribution on the surface of the subject, and a position of light irradiation on the surface of the subject,
wherein the processor is configured to:
acquire a first initial sound pressure distribution in the subject by using the first electrical signal,
acquire a second initial sound pressure distribution in the subject by using the second electrical signal,
set temporary values of the optical absorption coefficient and the optical scattering coefficient of the subject,
acquire a first temporary light intensity distribution of the first light in the subject and a second temporary light intensity distribution of the second light in the subject by using the temporary values,
acquire, as the optical absorption coefficient and the optical scattering coefficient of the subject, the temporary values when it satisfies the following equation (1), by an inverse iteration method using a first initial sound pressure value $P_1$ in the first initial sound pressure distribution at a specified position in the subject, a second initial sound pressure value $P_2$ in the second initial sound pressure distribution at the specified position, a first temporary light intensity value $\Phi_1$ in the first temporary light intensity distribution of the first light at the specified position, and a second temporary light intensity value $\Phi_2$ in the second temporary light intensity distribution of the second light at the specified position, and $$\frac{P_2}{P_1} = \frac{\Phi_2}{\Phi_1} \qquad (1)$$

acquire the information of the subject by using the first initial sound pressure distribution and the light intensity distribution of the first light.

2. The subject information acquisition apparatus according to claim 1, wherein the inverse iteration method is the least squares method using the first initial sound pressure value $P_1$ at the specified position, the second initial sound pressure value $P_2$ at the specified position, the first temporary light intensity value $\Phi_1$ of the first light at the specified position, and the second temporary light intensity value $\Phi_2$ of the second light at the specified position.

3. The subject information acquisition apparatus according to claim 2, wherein the processor is configured to acquire the first temporary light intensity distribution of the first light and the second temporary light intensity distribution of the second light for the case that an objective function of the least squares method is equal to zero or a value that can be considered as zero, as the light intensity distributions of the first light and the second light.

4. The subject information acquisition apparatus according to claim 3, wherein the value that can be considered as zero is equal to or smaller than $1.0 \times 10^{-6}$.

5. A subject information acquisition method using a processor for acquiring information of a subject relating to an optical absorption coefficient distribution by using a plurality of electrical signals due to a plurality of acoustic waves in response to irradiation of the subject with a plurality of lights, having a certain wavelength respectively, whose irradiation condition and irradiation time point are different from each other, the subject information acquisition method comprising:
acquiring an optical absorption coefficient and an optical scattering coefficient of the subject by using the plurality of electric signals;
acquiring a plurality of light intensity distributions of the plurality of lights in the subject, based on the optical absorption coefficient and the optical scattering coefficient of the subject acquired by using the plurality of electric signals; and
acquiring information of the subject relating to an optical absorption coefficient distribution by using the plurality of electrical signals and the plurality of light intensity distributions of the plurality of lights,
wherein the irradiation condition is at least one of a direction of light irradiation, an illumination distribution on the surface of the subject, and a position of light irradiation on the surface of the subject,
wherein the subject information acquisition method includes:
acquiring a first initial sound pressure distribution in the subject by using the first electrical signal,
acquiring a second initial sound pressure distribution in the subject by using the second electrical signal,
setting temporary values of the optical absorption coefficient and the optical scattering coefficient of the subject,
acquiring a first temporary light intensity distribution of the first light in the subject and a second temporary light intensity distribution of the second light in the subject by using the temporary values,
acquiring, as the optical absorption coefficient and the optical scattering coefficient of the subject, the temporary values when it satisfies the following equation (1), by an inverse iteration method using a first initial sound pressure value $P_1$ in the first initial sound pressure distribution at a specified position in the subject, a second initial sound pressure value $P_2$ in the second initial sound pressure distribution at the specified position, a first temporary light intensity value $\Phi_1$ in the first temporary light intensity distribution of the first light at the specified position, and a second temporary light intensity value $\Phi_2$ in the second temporary light intensity distribution of the second light at the specified position, and $$\frac{P_2}{P_1} = \frac{\Phi_2}{\Phi_1} \quad (1)$$

acquiring the information of the subject by using the first initial sound pressure distribution and the light intensity distribution of the first light.

6. A non-transitory storage medium storing a program causing a computer to execute each step of the subject information acquisition method according to claim 5.

7. The subject information acquisition apparatus according to claim 1, wherein the irradiation condition is a surface-illumination distribution on a surface of the subject.

8. The subject information acquisition apparatus according to claim 1, wherein the processor is configured to acquire the first temporary light intensity distribution of the first light in the subject by using a first illumination distribution of the first light on a surface of the subject and the temporary values, and configured to acquire the second temporary light intensity distribution of the second light in the subject by using a second illumination distribution of the second light on the surface of the subject and the temporary values.

9. The subject information acquisition method according to claim 5, wherein the inverse iteration method is the least squares method using the first initial sound pressure value $P_1$ at the specified position, the second initial sound pressure value $P_2$ at the specified position, the first temporary light intensity value $\Phi_1$ of the first light at the specified position, and the second temporary light intensity value $\Phi_2$ of the second light at the specified position.

10. The subject information acquisition method according to claim 9, wherein the method further includes acquiring the first temporary light intensity distribution of the first light and the second temporary light intensity distribution of the second light for the case that an objective function of the least squares method is equal to zero or a value that can be considered as zero, as the light intensity distributions of the first light and the second light.

11. The subject information acquisition method according to claim 10, wherein the value that can be considered as zero is equal to or smaller than $1.0 \times 10^{-6}$.

12. The subject information acquisition method according to claim 5, wherein the irradiation condition is a surface-illumination distribution on a surface of the subject.

13. The subject information acquisition method according to claim 5, wherein the method further comprises acquiring the first temporary light intensity distribution of the first light in the subject by using a first illumination distribution of the first light on a surface of the subject and the temporary values, and acquiring the second temporary light intensity distribution of the second light in the subject by using a second illumination distribution of the second light on the surface of the subject and the temporary values.

* * * * *